US008065162B1

(12) United States Patent
Curry

(10) Patent No.: US 8,065,162 B1
(45) Date of Patent: Nov. 22, 2011

(54) PROVIDER DATA MANAGEMENT AND CLAIMS EDITING AND SETTLEMENT SYSTEM

(75) Inventor: Bry Curry, Columbia, SC (US)

(73) Assignee: Blue Cross and Blue Shield of South Carolina, Columbia, SC (US)

( * ) Notice: Subject to any disclaimer, the term of this patent is extended or adjusted under 35 U.S.C. 154(b) by 1710 days.

(21) Appl. No.: 10/839,825

(22) Filed: May 6, 2004

Related U.S. Application Data

(60) Provisional application No. 60/468,870, filed on May 8, 2003.

(51) Int. Cl.
*G06F 17/60* (2006.01)
(52) U.S. Cl. .......................................................... 705/2
(58) Field of Classification Search ..................... 705/2
See application file for complete search history.

(56) References Cited

U.S. PATENT DOCUMENTS

| | | | |
|---|---|---|---|
| 5,704,044 A | 12/1997 | Tarter et al. | |
| 5,915,241 A | 6/1999 | Giannini | |
| 5,930,759 A | 7/1999 | Moore et al. | |
| 5,933,809 A | 8/1999 | Hunt et al. | |
| 5,956,690 A | 9/1999 | Haggerson et al. | |
| 5,991,750 A | 11/1999 | Watson | |
| 6,067,522 A | 5/2000 | Warady et al. | |
| 6,117,073 A | 9/2000 | Jones et al. | |
| 6,125,350 A | 9/2000 | Dirbas | |
| 6,182,047 B1 | 1/2001 | Dirbas | |
| 6,208,973 B1 * | 3/2001 | Boyer et al. ...................... 705/2 |
| 6,338,039 B1 | 1/2002 | Lonski et al. | |
| 6,341,265 B1 | 1/2002 | Provost et al. | |
| 6,343,271 B1 * | 1/2002 | Peterson et al. ................... 705/4 |
| 6,370,544 B1 | 4/2002 | Krebs et al. | |
| 7,072,842 B2 * | 7/2006 | Provost et al. ..................... 705/4 |
| 7,263,493 B1 * | 8/2007 | Provost et al. ..................... 705/4 |
| 2001/0027403 A1 * | 10/2001 | Peterson et al. ................... 705/4 |
| 2001/0034616 A1 | 10/2001 | Giannini | |
| 2001/0037224 A1 | 11/2001 | Eldridge et al. | |
| 2001/0051880 A1 | 12/2001 | Schurenberg et al. | |
| 2002/0019754 A1 | 2/2002 | Peterson et al. | |
| 2002/0022972 A1 | 2/2002 | Costello | |
| 2002/0077854 A1 | 6/2002 | Porterfield | |
| 2002/0091549 A1 | 7/2002 | Provost et al. | |
| 2002/0169955 A1 | 11/2002 | Bryant, Jr. et al. | |
| 2002/0198741 A1 * | 12/2002 | Randazzo ......................... 705/3 |
| 2004/0064386 A1 * | 4/2004 | Goguen et al. ................... 705/34 |

* cited by examiner

*Primary Examiner* — Gerald J. O'Connor
*Assistant Examiner* — Hiep V Nguyen
(74) *Attorney, Agent, or Firm* — B. Craig Killough

(57) ABSTRACT

A method and system of submitting healthcare claims for adjudication at the point of service is provided. The system provides methods and secure central storage for providers of healthcare services to maintain user created and maintained patient lists, provider location lists, and superbill forms for healthcare claims submission according to the user's unique and individual requirements. The system transmits completed healthcare claims while protecting patient privacy, and provides real-time adjudication of the claims, giving an almost instantaneous claim result in the form of a patient summary receipt back to the point of service at the healthcare provider's location. This is achieved through a real-time interface with the enterprise server claims adjudication engine. Customized lists and superbill forms as required by the individual user are also stored on the enterprise server.

31 Claims, 5 Drawing Sheets

Figure 1 - General Concept & Overview

*Figure 5*

Patient Summary Receipt

53
Date Completed: March 1, 2003  17

| | |
|---|---|
| Sponsor's SSN: | XXXXXX08 |
| Patient's Name: | DAWN B JONES |
| | 432 MAIN |
| | Anywhere, SC 29219 |
| Sponsor's Name: | DAVY A JONES |

} 54
} 1

| | |
|---|---|
| Services Provided by: | JOHN SMITH MD |
| Location: | OUR DOCTOR GROUP |
| | 123 MAIN STREEN |
| | ANYWHERE, SC 29222 |

} 55
} 2

| | |
|---|---|
| Claim Number: | XXXXXXXXX |
| Claim Status: | Complete |

} 56
} 3

*XPREJCLAIM™*

―――――――――――――57―――――――

| | |
|---|---|
| Dates of Service: | 07/24/02 through 07/24/02  58 |
| Claim Paid to: | OUR DOCTO60GROUP  5 |
| Total Billed: | $ 70.00  61 |
| TRICARE Allowed Amount: | $ 52.76  62 |
| Non-Covered Amount: | $ 17.24  63 |
| OHI Allowed Amount: | $ 0.00  64 |
| OHI Paid Amount: | $ 0.00  65 |
| Penalty Amount: | $ 0.00  66 |
| Amount Paid by Beneficiary: | $ 0.00  12 |
| | 67 |
| Amount Paid to DAWN B JONES: | $ 0.00  68 |
| Amount Paid to INTERNAL MED ASSC OF: | $ 39.57  69 |
| Total Amount Paid: | $ 39.57  15 |

*Patient Liability Summary*

| | |
|---|---|
| Patient's Deductible: | $ 0.00 |
| Patient's Cost-Share: | $ 13.19 |
| Patient's Copav: | $ 0.00 |

} 70
} 16

71  72  73  74  75

| 19 | 20 | 21 | 22 | 23 |
|---|---|---|---|---|
| Date of Service | Services Provided | Amount Billed | Allowed | Remarks |
| 07/24/02 | 99213 00 00 | $ 50.00 | $ 47.43 | CHARGES ARE MORE THAN ALLOWABLE AMOUNT. |
| 07/24/02 | 81000 00 00 | 20.00 | 5.33 | CHARGES ARE MORE THAN ALLOWABLE AMOUNT. |
| | | 77 | 78 | |
| | $ | 70.00 } 24 | $ 52.76 } 25 | |

} 76
} 18

79

80 Claim Number: XXXXXXXXX } 26

27 This is not an official Explanation of Benefits (EOB). In a few days, an official EOB will be available.

Ple81se note: In rare cases, some payment values may change between this receipt and the official EOB.
28

[Print this receipt]  [Close]

PROVIDER DATA MANAGEMENT AND CLAIMS EDITING AND SETTLEMENT SYSTEM

Applicant claims the benefit of Provisional Application Ser. No. 60/468,870 filed May 8, 2003.

BACKGROUND OF INVENTION

1. The Field of the Invention

The present invention relates to systems providing services that assist healthcare providers to manage their provider location data and their specific patient population data along with the capability to submit healthcare claims via the Internet and receive back an indication of the claim resolution. More specifically, registered healthcare provider representatives enter claims via the Internet and interact with the system to correct any claim entry errors so that claims can be adjudicated real-time. The present invention allows registered healthcare provider representatives to construct their own customized superbill for claim entry or use the standard claim entry Web pages available in the system. The system provides a patient summary receipt so that the registered healthcare provider representative knows the correct co-payment or cost share to collect from the patient at the point of service. The patient summary receipt also indicates the amount the healthcare provider will be paid.

2. Description of Prior Art

The administration of insurance claims represents a significant overhead in the overall cost of health care. The introduction of computers and the Internet and the adoption of standardized procedure and diagnosis codes has facilitated the claim submission and adjudication process. Nevertheless, the reliance by insurers and other third party payors and by health care providers on customized claim forms often necessitates the re-entry of patient and provider information and can result in erroneous entries. As a consequence, payments are delayed and processing overhead is increased.

Numerous proposals have been made for using the Internet in the processing of insurance claims, for example, Eldridge et al., U.S. Patent No. US 2001/0037224 A1; Boyer et al., U.S. Pat. No. 6,208,973 B1; Bryant, Jr. et al., U.S. Patent No. US 2002/0169955 A1; Moore et al., U.S. Pat. No. 5,930,759; and Tarter et al., U.S. Pat. No. 5,704,044. Further suggestions have been made specific to health care claims. Boyer et al., U.S. Pat. No. 6,208,973 B1, shows the use of a credit card to facilitate point of service payment and suggests using the Internet to transmit information about claims so that they may be adjudicated in real time. In a system described by Provost et al., U.S. Patent No. US 2002/0091549 A1 and Provost et al., U.S. Pat. No. 6,341,265 B1 when a potential claim is adjudicated and found to be not covered, the system provides information about the reason the claim is not covered and is may suggest an alternative service or treatment. Peterson, et al., U.S. Pat. No. 6,343,271 B1 and Peterson et al., U.S. Patent No. US 2002/0019754 A1 show a system that allows doctors to access patient information from a central database.

None of the prior art systems observed allow health care providers using the system at the point of service to access centrally stored information customized specifically for their practice without the use of specialized hardware or software.

SUMMARY AND OBJECTS OF THE INVENTION

The present invention relates to methods and systems for interactively submitting and resolving healthcare claims along with additional functions that assist with the management of data related to the healthcare claims submission process. According to the invention, healthcare provider representatives register to use the system via the Internet. The data each submits is authenticated against data located on the enterprise server system. Upon completion of the authentication process, registered healthcare provider representatives are authorized to submit healthcare claims via the Internet. Storing patient and provider data on a centralized enterprise server affords an added measure of security over the use of a web server database, as well as allowing efficient searching of large data files. The data is customized by the user, that is, the user creates the data and modifies the data from time to time according to the user's needs.

Using unique features such as provider created and maintained lists of their locations and patient population; the present invention enables registered healthcare provider representatives to submit healthcare claims through the system via the Internet. Selected claims edits are presented back to the registered healthcare provider representatives for online correction. When these edits cannot be resolved interactively is the claim is pended and will be resolved at a later date by operations staff at the healthcare payor's organization. The culminating result of the online claims submission process is real-time adjudication of a clean claim and the presentation to the registered healthcare provider representative of a patient summary receipt outlining charges submitted, allowable charges, amounts that will be paid to the provider and the patient's liability for services rendered.

Brief summaries of the provider data management functions in the present invention are described below. All functions and capabilities of the system are accessed via the Internet using a client computer. There is no need for office automation software on the client computer desktop; the only software requirement is a Microsoft or Netscape browser that meets the specified minimum browser requirements.

Customized Provider Location Lists

The system provides registered healthcare provider representatives the capability to create and maintain provider location lists. The system allows for selection and storage of provider locations associated with the registered healthcare provider's nine-digit provider tax identification number. Multiple lists can be created to accommodate different business and informational needs of the provider. The provider location lists are entered and maintained via the client's computer; they are, however, validated and stored on the enterprise server system.

Customized Patient Directory

The system provides registered healthcare provider representatives the capability to create and maintain their own specific patient directory. When a new healthcare provider registers, the system kicks off an automatic, one-time review of the provider's claims history on the enterprise server, which results in an initial population and storage of the provider's patient directory. Although this review is initiated through the web server, the actual data in the user's initial patient list and subsequent customized directory is maintained exclusively on the enterprise mainframe. This feature is particularly important in view of recent concerns and legislation regarding patient privacy. The system also allows registered healthcare provider representatives to add, update and delete patient records in this directory.

Important data such as the patient account number can be added to the patient directory. If a provider office or facility consists of several locations, the patient account number for each location can be stored as well. A search feature is available and provides searches on patient name or account number. This is helpful for locating a patient on a large directory and to narrow the selection list. The registered healthcare provider representative first selects their location from their "Locations List." In certain instances, specific provider specialties will require the selection of the provider that rendered the service. In such cases, the system automatically provides the list of affiliated rendering providers, thereby making the selection process more efficient. The system then retrieves the patient records from the user's customized "Patient Directory" that have accounts at the selected location. The system displays a summary list of the patients, showing the patients' names and account numbers. When using the system to submit healthcare claims, the records on the user's Patient Directory are used to automatically populate patient data on the claim. This reduces keying errors and provides office efficiency for the healthcare claims entry process.

Customized Superbill Form for Healthcare Claim Submission

The present invention provides two methods for healthcare claims submission. A user, such as a registered healthcare provider representative, can elect to construct a customized superbill using the systems' superbill option, and then use that customized superbill for claims entry, or can elect to use the standard Web pages for claims entry. The superbill option allows registered healthcare provider representatives to easily design custom superbills to use for entering claim information to be submitted via the Internet to the enterprise server system. The customized superbill, tailored to the healthcare provider's needs, becomes the format for submission of the healthcare claim via the Internet.

To build a custom superbill the registered healthcare provider representative selects the procedure codes and diagnosis codes routinely used in their practice. The procedure codes and diagnoses codes are authenticated against the enterprise server system for validity before being stored. Once the provider has stored their most frequently used and important codes, the codes will be displayed back for claims entry in a "look-and-feel" similar to the paper superbill which they are accustomed to using in their office practice. The customized superbill is also stored on the enterprise server system. Since there are literally thousands of recognized procedure codes that may be used on claim forms, the use of a customized electronic form, or "superbill" offers significant advantages. By allowing healthcare providers the option of entering claim information in this manner for submission via the Internet, the present invention increases the efficiency of claims submission and reduces potential errors in keying invalid codes in the claims submission process.

When a registered healthcare provider representative selects the "Superbill" option for claims submission, the enterprise server retrieves data and presents the customized display with the previously stored codes. After selecting the provider billing location, rendering physician, if applicable, and patient specific to the associated charges, the provider will identify the diagnosis associated with the charges and select procedures from their customized Superbill for which they have charges and the number of units for each procedure being billed along with the charge for each selected procedure. Once the appropriate claim data has been entered (that data may include billing location, rendering provider information, patient information, procedures and charges), the data is passed via the Internet to the real-time claims adjudication enterprise server engine.

Patient Summary Receipt

Once the claims information is processed the real-time claim result is sent back and presented on the client's computer in the form of the "Patient Summary Receipt" (PSR). The PSR shows a summary overview of the claim information submitted and how those services and charges were adjudicated by the enterprise server claims processing engine. Pertinent patient information, provider location and rendering information and the services and charges submitted on the associated claim are shown on the PSR. The receipt also displays the amount the provider will be reimbursed and the amount the patient should pay.

The PSR also presents a service-by-service overview that compares the amounts the provider billed, the amounts the payor allowed and any remarks to explain differences between the amounts billed and the amounts allowed. Included in the PSR claim's processing overview is a disclaimer informing the provider that at times some payment values or amounts may differ between the PSR and the official Explanation of Benefits (EOB) or remittance. The official Explanation of Benefits and provider remittances are documents that are produced during backend settlement processes that occur on the enterprise server engine after the PSR real-time adjudication is completed.

The invention, which automates real-time, online adjudication along with the unique provider data storage and management functions for Provider Location Lists, Patient Directory and customized creation of a superbill form for claims entry, provides significant advantages for providers submitting healthcare claims in today's environment. The real-time adjudication and Patient Summary Receipt help providers manage the collection of the correct amounts owed by their patients at the point of service. This eliminates costly follow-up billing to collect money owed by patients. The Provider Location List and Patient Directory functions provide quicker claims entry by using selection functionality, thereby avoiding keying errors on critical patient data and provider location data. The systems' option of offering the customized superbill as the claims entry method also provides for a more efficient and accurate submission of critical healthcare claims data such as the specific procedures and diagnosis codes that are a typical requirement for healthcare claims adjudication. The objects and features of the invention are described in more detail in the following sections.

DESCRIPTION OF THE DRAWINGS

In order to further describe the invention and clearly depict the advantages of the invention accompanying drawings will explain with additional specificity and detail the use and operation of the invention. These drawings depict only typical embodiments and should not therefore be considered limiting of the scope of the invention.

FIG. 5 is an illustration of the Patient Summary Receipt that the system provides back to the healthcare provider upon successful resolution of a healthcare claim.

DETAILED DESCRIPTION OF THE PREFERRED EMBODIMENTS

The described embodiments should be considered as illustrative and not limiting.

Figure 1:
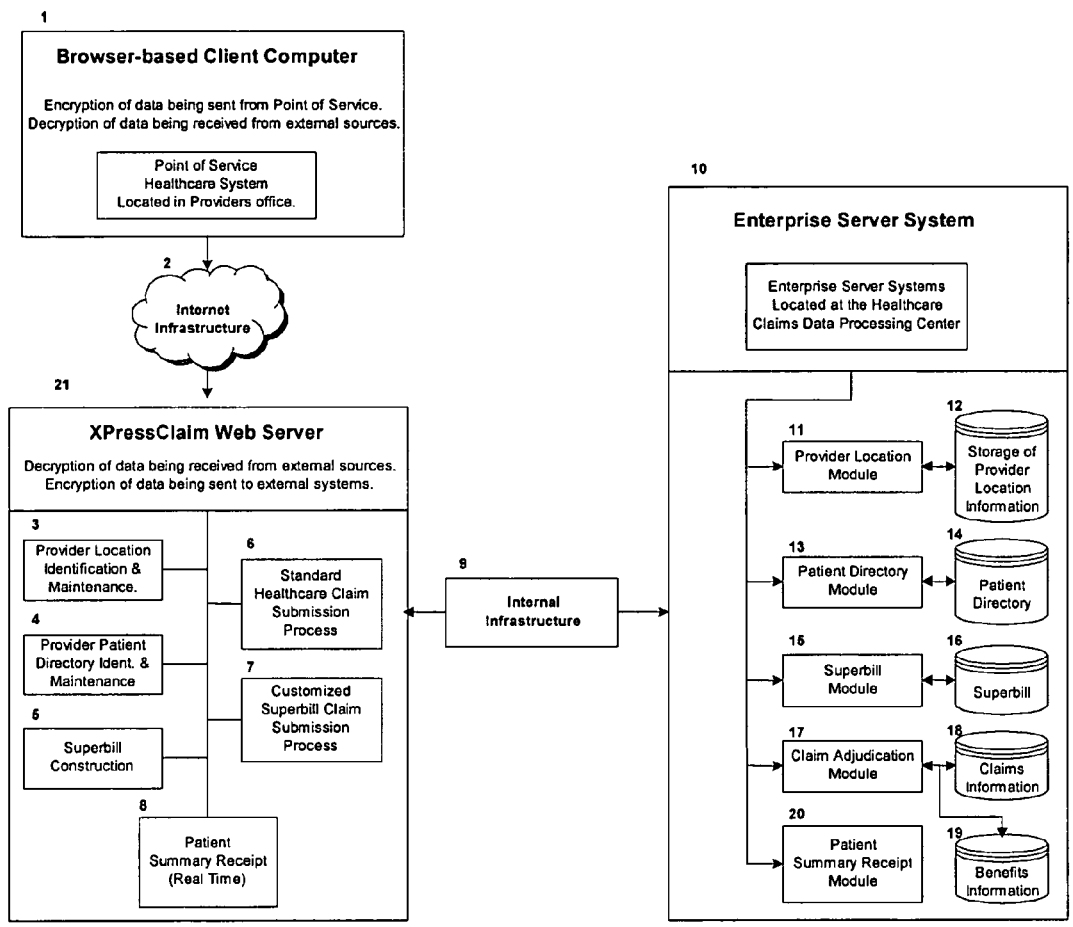
FIG. 1 is a schematic diagram illustrating the interactive system according to the invention including the client point of service claim entry process along with unique provider location list management and patient directory management, Internet encryption process, enterprise server system process at the healthcare claims processing data center, and the real-time claims adjudication process that results in the subsequent return of a patient summary receipt to the healthcare provider.

FIG. 1 illustrates an overview of the invention. Through an Internet service provider (ISP) connection to the Internet 2 and the browser on the provider representative's client computer 1, the registered healthcare provider representative accesses a series of functions, implemented on interface server 21, to support submission of healthcare claims for real-time adjudication and management of other provider functions utilized to support the claims submission process.

The registered healthcare provider representative maintains a list of provider locations, using the corresponding interface function 3, for the provider organization. This list is stored on the enterprise server system 10 in data store 12. A provider location module 11 retrieves current provider location data from the enterprise server provider database, and allows the registered healthcare provider representative to select locations to build customized locations lists to suit individual business needs of the provider representative.

The registered healthcare provider representatives for a provider organization maintain a Patient Directory of patients served by the provider organization, using the corresponding interface function 4. This directory is stored on the enterprise server system 10 in data store 14. Based on identifying information entered by the registered healthcare provider representative, a Patient Directory module 13 retrieves current patient data from the enterprise server patient database 14, and allows the provider representative to add a patient record to the provider organization's Patient Directory. The maintenance function 4 also accepts entry of the patient's account number specific to a provider location, for storing in the Patient Directory 14. In addition, the Patient Directory module 13 helps a newly registered provider organization by pre-loading their Patient Directory with records for patients from their prior 12-months claims history, from is the enterprise server claims history database 18.

Using interface function 5, the registered healthcare provider representative has the option to create a Superbill and customize it with the specific diagnosis codes and procedure codes most important and most often used on the healthcare claims submitted by the provider organization. The customized superbill is stored on the enterprise server system 10 in data store 16. A Superbill module 15 validates codes entered by the provider representative and allows the provider representative to add and remove codes as necessary.

The data provided by the user, as described above, is customized, that is, the user provides the data to the enterprise server system and modifies the data from time to time according to the user's needs. The data is proprietary to the user, and is amended or modified by the user, and not by the owner or administrator of the enterprise server, or by the third party payer. The data is therefore under the control of the user, and is maintained by the user, even though it is stored on the enterprise server.

To submit a healthcare claim online through the Internet 2, the registered healthcare provider representative uses these functions to make quick selections from the lists they have maintained and to automatically populate data fields on the claim with data stored for these selections. First, the provider representative identifies and selects the provider location from registered healthcare provider representative's customized provider location list stored in data store 12. Next the provider representative identifies and selects the patient from the provider organization's Patient Directory, stored in data store 14, for the selected location. Because these data stores are maintained on the enterprise server, a high degree of security is ensured.

Next, the provider representative selects whether to use the Standard Healthcare Claim Submission process 6 or the Customized Superbill Claim Submission process 7. If the Standard Healthcare Claim Submission process 6 is selected, the provider representative enters all the claim line data on the system's Web claim entry pages. If the Customized Superbill Claim Submission process 7 is selected, the claim entry form on the Web page will appear in the same "look and feel" as the paper Superbill, using the Superbill constructed for the provider organization and stored in data store 16. The provider representative will select diagnosis codes and procedures listed on the Superbill.

Once all selections and claim line entry are complete, the healthcare claim is submitted. All data collected from the provider location selection 3, Patient Directory selection 4, Superbill entry 7 or standard claim line entry 6, are passed to the Claim Adjudication module 17 on the enterprise server system. Benefit information on the enterprise server stored in data store 19 for the patient is retrieved to determine how to adjudicate the claim. The processed claim is stored on the claims database 18 on the enterprise server. Again, a high standard of security is achieved by using the enterprise server for storage of claim information.

When the claim processes completely, the Patient Summary Receipt module 20 generates the Patient Summary Receipt 8, which is displayed on the Web response page to the registered healthcare provider representative. The Patient Summary Receipt includes the claim number assigned to the claim along with line-by-line detail of the submitted charges and how the charges will be reimbursed. It also indicates the amounts for which the patient is liable. The Patient Summary Receipt 8 can be printed on the provider representative's client computer for immediate presentation to the patient.

Figure 2:
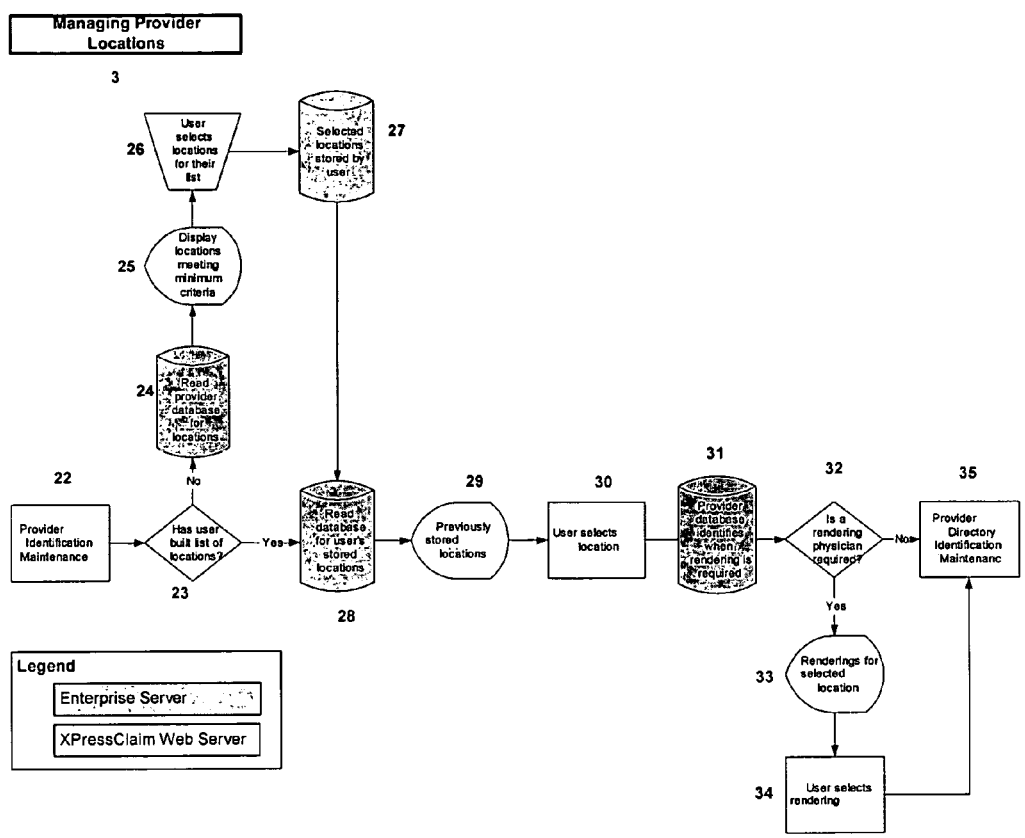
FIG. 2 is a schematic diagram illustrating the key healthcare provider or healthcare provider billing representative interactions specific to the provider location definition and maintenance, and the additional interaction of the healthcare provider or designated billing representative and patient population lists.
Figure 3:
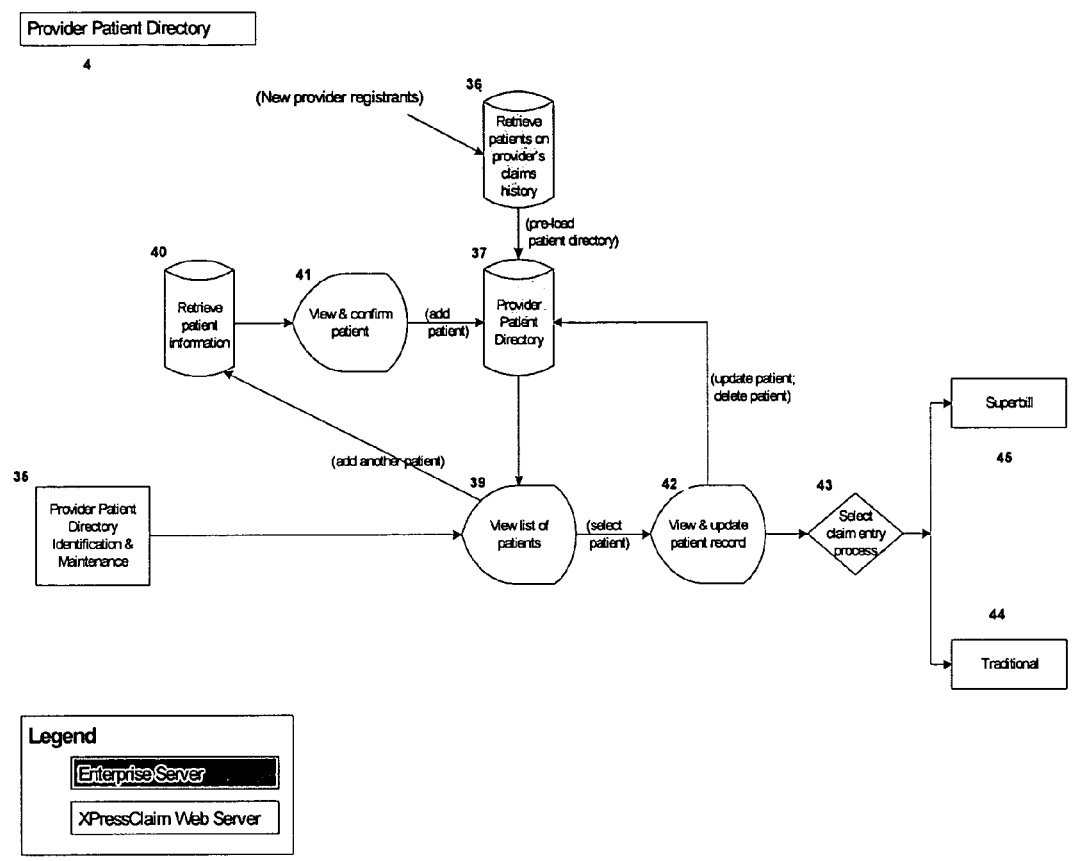
FIG. 3 is a schematic diagram illustrating one embodiment of the methods of the invention that provides the capability for management of a specific patient population list known as the Patient Directory.
Figure 4:
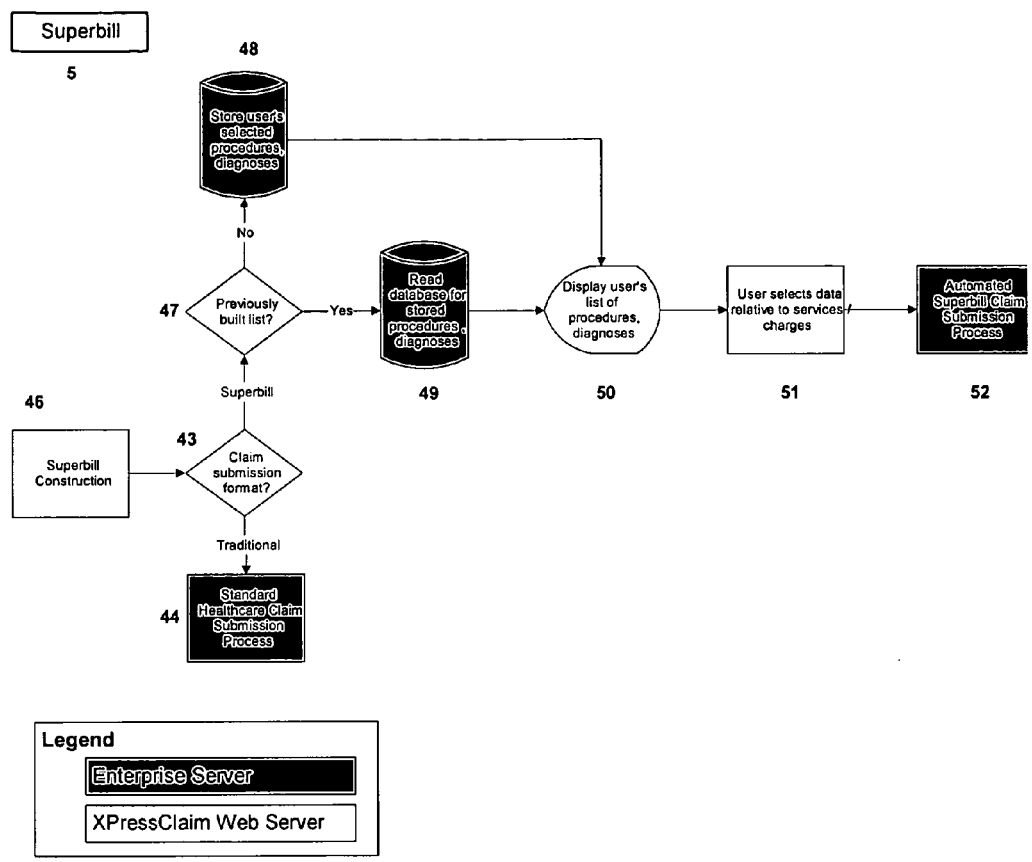
FIG. 4 is a flow diagram depicting one embodiment of the methods of the invention for entering the healthcare claims using the Superbill option or the standard Web pages.

Internal infrastructure 9 between interface server 21 and data server 10 is shown in greater detail in FIGS. 2-4. In particular, elements from interface server 21 are shown unshaded, while elements from data server 10 are shaded in FIGS. 2-4.

FIG. 2 shows a flowchart illustrating one embodiment of the interface function 3 of the present invention that registered healthcare provider representatives use to create, maintain and manage their provider locations list(s). The registered healthcare provider representative (user) is first presented with a starting screen 22. In order to create or maintain a list of billing locations, the interface server initiates a query operation 24, in turn executed by Provider Location module 11, whereby provider databases 12 on the enterprise server are interrogated. Locations found during that interrogation meeting minimum criteria are displayed to the user at step 25. The user may then, at step 26, select and add to their customized provider location list(s). Update query 27 is executed to store the selected locations by username in the internal database 12 on the enterprise server 10 so that they will be available for repeated retrieval.

The system allows the ability to create multiple lists in order to give the process flexibility and uniqueness for each registered healthcare provider representative. The user can organize multiple locations into logical lists, for example if the user is a billing clerk for multiple locations, then one list could be created for their general practitioners, another list for their internists and a third list for their laboratories.

If the user has previously created one or more provider location lists and does not wish to update them, branch operation 23 proceeds to query 28. Locations that have been stored to those location lists for repeated use are then displayed at step 29. All provider data is stored and retrieved from the enterprise server 10 by means of provider location module 11. Once the location list(s) are displayed, the user identifies, at input selection step 30, the specific billing location associated with the claim being submitted. Query 31 is then initiated to determine whether the selected location from the list meets criteria requiring that the individual physician who rendered or performed the services be identified. If these criteria are not met, branch operation 32 proceeds directly to the starting screen 35 for the Patient Directory Identification and Maintenance process 4. Otherwise, physicians employed by the selected billing location, as determined by query 31, are displayed at step 33. The submitting user then selects from the displayed physicians at input selection step 34 and is then routed to their Patient Directory screen 35 where the claim's patient is selected. The registered healthcare provider representative then continues with the process to enter claim information that will be submitted via the Internet to the enterprise server for adjudication.

FIG. 3 shows a flowchart illustrating one embodiment of the methods implementing interface function 4 of the present invention, which allows registered healthcare provider representatives to manage the Patient Directory. In FIG. 3, the Patient Directory for a user's provider organization is preloaded when the provider organization first registers to use the system to submit healthcare claims via the Internet. The provider organization's prior 12 months' claims history on the carrier's claims history database 18 is examined at query step 36 to retrieve information for the provider organization's patients for which the provider organization has filed claims to the carrier. This information includes each patient's name, address, and carrier patient ID. One base record for each patient is loaded to the Patient Directory for the provider organization based on provider Tax Identification Number (TIN). All claims history data is interrogated on the enterprise server 10. The patient data retrieved by query 36 and loaded into the user's Patient Directory is also stored on enterprise server 10 by means of update query 37. The registered healthcare provider representative accesses the Patient Directory information using a standard Internet web browser application on the client computer 2 and accesses the information through the Internet. No office automation software is required on the client computer 2. Further, in accordance with the present invention, while the update and retrieval queries for patient information and other data are initiated through interface server 21, the data are stored only on enterprise server 10, rather than on the interface server 21. Thus, enterprise server 10 need not be directly connected to the Internet and the patient information and other data stored there can be more readily protected from unauthorized access.

Prior to initiating the Patient Directory Identification and Maintenance process 4, the user will have identified the provider location for which inquiries and claims entry will be done. Upon displaying the starting screen (Web page) 35 for the Patient Directory Identification and Maintenance process 4, the system retrieves and displays a summary list of the patient records 39 from the Patient Directory for the selected provider location. The user then has the option to select a patient on the summary list and proceed to enter claim information, or to add a new patient record on the Patient Directory.

If the user chooses to add a new patient record, identifying data for the patient is entered on the Web page. Using the identifying data, the system first determines whether that patient's base record already exists on the Patient Directory for the provider organization. If it does, the system displays the record on confirmation screen 41 for verification by the user. Once the provider representative confirms the patient, updates can be made to the base information and the patient's account number specific to the provider location can be entered. Then the system adds the provider location to the Patient Directory for the patient, and executes update query 37 to save the revisions or corrections on the enterprise server database.

When adding a new patient record, if the system does not find a base record for the patient for the provider organization, the system queries the enterprise server patient databases 40 to retrieve current information about the identified patient. The information thus retrieved is displayed back to the user to view and confirm on screen 41, just as for base records found in the provider's Patient Directory. If no patient information is found, the user can modify the identifying data to try again. If more than one patient is found, such as a set of twins, the user selects the one that is appropriate. Once the user confirms the correct patient information has been retrieved, the patient's account number specific to the provider location can be entered. Then the system adds the base record for the patient to the Patient Directory, along with the selected provider location. All data is updated 37 on the enterprise server 10.

When the user selects a patient from the summary list of patient records displayed at 39, after updating the Patent Directory as necessary, the system displays a patient detail screen 42 (Web page) showing the selected patient's detail data from the Patient Directory 2 for the provider representative to view. On this Web page, the user can enter updates to the patient's record on the provider's Patient Directory, including patient address and patient account number specific to the provider location. Again, the any such modifications to the patient's detail data in the provider's patient Directory are updated on the enterprise server 10 at query step 37.

After viewing the patient's detail data, the registered healthcare provider representative can also choose to delete the patient record from the Patient Directory. The selected provider location is deleted from the Patient Directory; the patient's base record for the provider organization remains.

Once the patient record from the Patient Directory is confirmed, the patient's data is carried forward by the system to automatically populate applicable data items in the claims entry process. At branch step 43, the user chooses whether to enter the claim via the standard claim submission screen 44 or the superbill claim submission screen 45.

FIG. 4 shows a flowchart illustrating one embodiment of interface function 7 of the present invention, which allows users to create an electronic form similar to their paper superbills that are used in their offices. In the present invention, the customized superbill is one option available for entering the claim data that will be submitted for real-time claims adjudication. In the healthcare industry, a superbill is a paper form that administrative staff at provider offices often use to code and capture procedures, diagnoses and charges for services rendered to their patients. These forms are printed by various vendors and contain codes that an individual provider office uses most often. In an effort to give the registered healthcare provider representatives submitting charges through the present system a format they are familiar with, this invention provides a method of capturing the provider's most often used procedure and diagnosis codes and displaying those codes on the Web page claim entry screens similar to the way their paper superbills are laid out.

As registered users access the claim entry function in this system, the system provides the option of submitting their claim through either a traditional format or through a superbill format. If the registered healthcare provider representative selects the superbill format they will initially create their superbill to be used by means of superbill construction screen 46. The user identifies the procedure and diagnoses codes that appear on the provider's paper superbill. Those codes will be stored, via update query 48, on the enterprise server by the registered provider's username (the ID they use along with their password to access the application.) If the registered healthcare provider representative has previously built their superbill, branch operation 47 proceeds to query 49, retrieving the procedure and diagnosis codes stored by the provider from the enterprise server 10. Once the enterprise server has been read the procedure and diagnosis codes are retrieved and displayed on the superbill screen 50 on the client's computer in a format that looks similar to the layout of a paper superbill. The browser superbill 50 allows the user to select services rendered, quantities and charges for each service, and one or more diagnoses relative to the episode of care being billed via the system, as shown at step 51. Once the registered healthcare provider representative selects and enters the codes and charges for the specified claim, the claim information is submitted via the Internet and the data is sent, as shown at step 52, to the enterprise server 10 for adjudication.

FIG. 5 illustrates the Patient Summary Receipt (PSR). The PSR is created for claims that complete their processing during the session in which they were keyed and while the actual explanation of benefits (EOB) and provider remittance will be generated as appropriate in later processing of the system, the PSR gives an immediate summary of how a claim adjudicated.

The date 53 shown on the PSR coincides with the date that the claim processed. Sponsor and Patient specific name and address information 54 is included to aid in associating the correct claim and PSR together. As a privacy and security feature, the Sponsor's social security number is masked instead of displayed. Also, to assist the registered healthcare provider representative in allocating the PSR to the correct 55 are included.

Claim specific information is shown in the body of the PSR. The claim number and completed status 56 give the registered healthcare provider representative a number to reference if customer service should need to be contacted with questions. Included in the detailed PSR information are the date(s) of service 57 for the submitted charges and the office location 58 that will receive reimbursement for the submitted charges.

Various dollar amounts are included in the PSR to explain the charge(s) submitted and how the charge(s) will be reimbursed. The PSR shows the total amount 60 that was billed. The total is an accumulation of all claim lines that were submitted by the registered healthcare provider representative using the system. The allowed amount 61 relative to the submitted charges is displayed on the PSR since there is usually a difference between what a registered healthcare provider representative bills for a service and the amount that is reimbursable contractually. The difference between those two amounts is referred to as the non-covered amount 62. When submitting charges for reimbursement, the billing provider representative identifies the amount, if any, the other health insurance (OHI) carrier allowed 63 and paid 64. Those amounts are taken into consideration when actual reimbursement is calculated.

Occasionally, there are situations where a penalty 65 is applied to any reimbursement that will affect the amount(s) paid to the provider, patient or both. Also taken into consideration before payments are issued is any prior payment made by the patient 66.

Taking the services provided, and prior payments and contractual rates into consideration, the amounts paid out to the patient 67 and provider 68 are shown and then totaled to show the amount expected to be reimbursed 69.

In an effort to prevent the patient from being billed for any non-covered amounts or amounts for which they are not responsible, the PSR shows the amount(s) 70 the patient is expected to pay themselves, identified as their deductible, cost-share and copay amounts.

Below the summary section of the PSR is a detailed line-by-line itemization 76 of the claim information that was submitted for processing. The date of service 71 for each line is shown along with the services 72 or procedure codes and each associated line charge billed 73. For each billed amount, the PSR shows the associated allowed amount 74 and any relative remarks 75 that would explain how or why a charge was reimbursed as it was. Also, the total charge for all submitted charges 77 and the total allowed amount 78 are shown again at the bottom of the line breakdown, and the claim number 79 is displayed again.

Two disclaimers are included at the bottom of the PSR. One disclaimer 80 states that the PSR is not an official Explanation of Benefits (EOB) and that the actual EOB will be available on the Web. The other disclaimer 81 informs the registered healthcare provider representative that the reimbursement indicated on the PSR may not reflect the actual reimbursed amounts due to circumstances not identifiable at the time of the completion of the online processing.

What is claimed is:
1. A method of managing healthcare provider data and preparation and settlement of healthcare provider claims, said method comprising the steps of:
  a) creating provider location data in a provider location module, wherein said provider location module is on an enterprise server at a location that is remote from a provider with whom the provider location data is associated, and said provider location data comprises a list of provider locations of the provider, and a list of health care professionals associated with each of said provider locations, wherein provider location data is presented by the enterprise server to the provider for preparation of a healthcare claim;
  b) creating a patient directory in a patient directory module, wherein said patient directory module is present on the enterprise server at a location that is remote from the provider, and wherein the patient directory comprises a plurality of patient names, a patient number unique to each patient name assigned to each patient name of said plurality of patient names, claims histories associated with patient names, and a third party payer associated with each patient name and patient number, wherein data from the patient directory is presented by the enterprise server to the provider for preparation of the healthcare claim;

c) creating a superbill module, wherein said superbill module is present on the enterprise server at a location that is remote from the provider, wherein said superbill module comprises a list of diagnosis codes and a list of treatment codes uniquely associated with each provider location of the provider, and a charge amount for each diagnosis code of the list of diagnosis codes and a charge amount for each treatment code of the list of treatment codes, wherein data from the superbill module is presented by the enterprise server to the provider for preparation of the healthcare claim;

d) the enterprise server preparing the healthcare claim, wherein the enterprise server provides to a user acting on behalf of the healthcare provider at a location that is remote from the enterprise server, the list of provider locations of the healthcare provider, and the user selects a provider location from the list of provider locations at which the provider has provided healthcare services for which the healthcare claim is submitted, and wherein the enterprise server presents to the user the patient directory for the selected provider location, and the user selects a patient identifier from the patient directory, and wherein the enterprise server presents the user with the list of health care professionals associated with the selected provider location, and the list of diagnosis codes and the list of treatment codes associated with the selected provider location, and the user selects a health care professional from the list of health care professionals associated with the selected provider location, and the user selects a diagnosis from the list of diagnosis codes and a treatment from the list of treatment codes associated with the selected provider location;

e) the user confirming the healthcare claim to the enterprise server;

f) adjudicating the healthcare claim in real time, wherein adjudicating the healthcare claim comprises the steps of determining the amount of money to be paid to the provider by a third party payer, and determining the patient's financial responsibility to the provider; and g) presenting to the user in real time a patient summary receipt, said patient summary receipt comprising information on charges submitted for adjudication, charges allowed to the provider by the adjudication, amounts of money to be paid to the provider by the third party payer, and the patient's financial responsibility to the provider.

2. A method of managing healthcare provider data and preparation and settlement of healthcare provider claims as described in claim 1, wherein use of the enterprise server is shared by other healthcare providers, but said other healthcare providers may not access the provider location module or the patient directory module of the healthcare provider.

3. A method of managing healthcare provider data and preparation and settlement of healthcare provider claims in real time as described in claim 2, wherein use of the enterprise server is shared by other healthcare providers, but said other healthcare providers may not access the superbill module or the list of diagnosis codes or the list of treatment codes of the provider.

4. A method of managing healthcare provider data and preparation and settlement of healthcare provider claims as described in claim 1, wherein use of the enterprise server is shared by other healthcare providers, but said other healthcare providers may not access the superbill module or the list of diagnosis codes or the list of treatment codes of the provider.

5. A method of managing healthcare provider data and preparation and settlement of healthcare provider claims as described in claim 1, wherein the patient summary receipt provides remarks explaining differences in third party payment responsibility and the amount of the healthcare claim as submitted by the enterprise server.

6. A method of managing healthcare provider data and preparation and settlement of healthcare provider claims as described in claim 1, further comprising the steps of the enterprise server comparing the list of diagnosis codes with standard diagnosis codes and the list of treatment codes with standard treatment codes, and the enterprise server validating each diagnosis code of the list of diagnosis codes and each treatment code of the list of treatment codes prior to entering the list of diagnosis codes and the list of treatment codes into said superbill module.

7. A method of managing healthcare provider data and preparation and settlement of healthcare provider claims as described in claim 1, wherein the user confirms the healthcare claim to the enterprise server from the provider location via the internet.

8. A method of managing healthcare provider data and preparation and settlement of healthcare provider claims as described in claim 1, wherein the enterprise server causes funds for payment of the healthcare claim to be tendered to the provider substantially contemporaneously with the adjudication of the healthcare claim.

9. A method of managing healthcare provider data and preparation and settlement of healthcare provider claims, as described in claim 1, further comprising the step of periodically deleting patient names and adding patient names to the patent directory module.

10. A method of managing healthcare provider data and preparation and settlement of healthcare provider claims, as described in claim 1, wherein the healthcare claim prepared by the enterprise server comprises the selected provider location, the selected patient name and patient number, the selected health care professional, the selected diagnosis code and the selected treatment code, and wherein the enterprise server associates charges with the selected diagnosis code and the selected treatment code and prepares charges for payment adjudication.

11. A method of managing healthcare provider data and preparation and settlement of healthcare provider claims, as described in claim 1, wherein a claims adjudication module of the enterprise server compares the healthcare claim with rules for payment associated with a third party payer selected by the enterprise server from a database comprising rules for payment of multiple third party payers, and wherein the third party payer is associated for payment of the healthcare claim with the patient name and patient number for which the healthcare claim is submitted.

12. A method of managing healthcare provider data and preparation and settlement of healthcare provider claims as described in claim 1, wherein the enterprise server provides to the user acting on behalf of the healthcare provider at the location that is remote from the enterprise server, the list of provider locations of the healthcare provider, the list of health care professionals associated with the selected provider location, and the list of diagnosis codes and the list of treatment codes associated with the selected provider location via the internet.

13. A method of managing healthcare provider data and preparation and settlement of healthcare provider claims as described in claim 1, wherein the enterprise server is maintained at a physical location operated by the third party payer.

14. A method for managing healthcare provider data and preparation and settlement of healthcare provider claims, said method comprising the steps of:

a) creating a provider patient directory module comprising a patient directory that is unique to a healthcare provider, wherein said patient directory module is present on an enterprise server at a location that is remote from the healthcare provider, wherein the patient directory comprises data comprising a plurality of patient names, a patient number unique to each patient name and assigned to each patient name of said plurality of patient names, and a third party payer associated with each patient name and patient number;

b) creating a provider superbill module, wherein said superbill module is present on the enterprise server at a location that is remote from the healthcare provider, wherein said superbill module comprises data comprising a list of diagnosis codes and a list of treatment codes uniquely associated with a provider location of the healthcare provider as selected by the healthcare provider, and wherein a charge amount is associated with each diagnosis code of the list of diagnosis codes and a charge amount is associated with each treatment code of the list of treatment codes;

c) the enterprise server preparing a healthcare claim for the healthcare provider, wherein the enterprise server assembles data from the patient directory module and data from the superbill module that is associated with the provider location to populate a claim form and the enterprise server transmits the data so assembled from the patient directory module and from the superbill module to a provider computer at a provider location that is remote from the enterprise server, and wherein the enterprise server presents to a user the patient directory for the provider location, and the user selects a patient identifier from the patient directory, and wherein the enterprise server presents the user with a list of health care professionals associated with the provider location, and the list of diagnosis codes and the list of treatment codes associated with the provider location, and the user selects a health care professional from the list of health care professionals associated with the selected provider location, and the user selects a diagnosis from the list of diagnosis codes and a treatment from the list of treatment codes associated with the selected provider location;

d) the user confirming the healthcare claim to the enterprise server; and e) adjudicating the healthcare claim.

15. A method for managing healthcare provider data and preparation and settlement of healthcare provider claims, as described in claim 14, said method further comprising the steps of adjudicating the healthcare claim in real time, wherein adjudicating the healthcare claim comprises the steps of determining the amount of money to be paid to the provider by a third party payer in real time, and determining the patient's financial responsibility to the provider in real time.

16. A method for managing healthcare provider data and preparation and settlement of healthcare provider claims, as described in claim 14, said method further comprising the steps of:

adjudicating the healthcare claim in real time, wherein adjudicating the healthcare claim comprises the steps of determining the amount of money to be paid to the provider by a third party payer in real time, and determining the patient's financial responsibility to the provider in real time; and transmitting to the provider computer in real time a patient summary receipt, said patient summary receipt comprising information on charges submitted for adjudication, charges allowed to the provider by the adjudication, amounts of money to be paid to the provider by the third party payer, and the patient's financial responsibility to the provider.

17. A method for managing healthcare provider data and preparation and settlement of healthcare provider claims, as described in claim 14, said method further comprising the steps of creating provider location data for use by a provider in a provider location module, wherein said provider location module is on a enterprise server at a location that is remote from a provider with whom the provider location data is associated, and said provider location data comprises a list of provider locations of the provider, and a list of health care professionals associated with each of said provider locations wherein the enterprise server assembles data from the provider location module to populate the claim form and the enterprise server transmits the data so assembled to the provider computer with the data so assembled from the patient directory module, and a user acting on behalf of the healthcare provider selects a provider location from the list of provider locations.

18. A method for managing healthcare provider data and preparation and settlement of healthcare provider claims, as described in claim 14, wherein the patient directory module comprises data claims histories associated with the patient names.

19. A method for managing healthcare provider data and preparation and settlement of healthcare provider claims, as described in claim 14, wherein the enterprise server presents to the user the patient number assigned to the patient name selected by the user, and the third party payer associated with the patient name selected by the user.

20. A method of managing healthcare provider data and preparation and settlement of healthcare provider claims as described in claim 14, wherein use of the enterprise server is shared by other healthcare providers, but said other healthcare providers may not access the provider location module or the patient directory module of the healthcare provider.

21. A method of managing healthcare provider data and preparation and settlement of healthcare provider claims in real time as described in claim 20, wherein use of the enterprise server is shared by other healthcare providers, but said other healthcare providers may not access the superbill module or the list of diagnosis codes or the list of treatment codes of the provider.

22. A method of managing healthcare provider data and preparation and settlement of healthcare provider claims as described in claim 14, wherein use of the enterprise server is shared by other healthcare providers, but said other healthcare providers may not access the superbill module or the list of diagnosis codes or the list of treatment codes of the provider.

23. A method of managing healthcare provider data and preparation and settlement of healthcare provider claims as described in claim 14, wherein the patient summary receipt provides remarks explaining differences in third party payment responsibility and the amount of the healthcare claim as submitted by the enterprise server.

24. A method of managing healthcare provider data and preparation and settlement of healthcare provider claims as described in claim 14, further comprising the steps of the enterprise server comparing the list of diagnosis codes with standard diagnosis codes and the list of treatment codes with standard treatment codes, and the enterprise server validating each diagnosis code of the list of diagnosis codes and each treatment code of the list of treatment codes prior to entering the list of diagnosis codes and the list of treatment codes into said superbill module.

25. A method of managing healthcare provider data and preparation and settlement of healthcare provider claims as described in claim 14, wherein the user confirms the healthcare claim to the enterprise server from the provider location via the internet.

26. A method of managing healthcare provider data and preparation and settlement of healthcare provider claims as described in claim 14, wherein the enterprise server causes funds for payment of the healthcare claim to be tendered to the provider substantially contemporaneously with the adjudication of the healthcare claim.

27. A method of managing healthcare provider data and preparation and settlement of healthcare provider claims, as described in claim 14, further comprising the step of periodically deleting patient names and adding patient names to the patent directory module.

28. A method of managing healthcare provider data and preparation and settlement of healthcare provider claims, as described in claim 14, wherein the healthcare claim prepared by the enterprise server comprises the selected provider location, the selected patient name and patient number, the selected health care professional, the selected diagnosis code and the selected treatment code, and wherein the enterprise server associates charges with the selected diagnosis code and the selected treatment code and prepares charges for payment adjudication.

29. A method of managing healthcare provider data and preparation and settlement of healthcare provider claims as described in claim 14, wherein a claims adjudication module of the enterprise server compares the healthcare claim with rules for payment associated with a third party payer selected by the enterprise server from a database comprising rules for payment of multiple third party payers, and wherein the third party payer is associated for payment of the healthcare claim with the patient name and patient number for which the healthcare claim is submitted.

30. A method of managing healthcare provider data and preparation and settlement of healthcare provider claims as described in claim 14, wherein the enterprise server provides to the user acting on behalf of the healthcare provider at the location that is remote from the enterprise server, the list of provider locations of the healthcare provider, the list of health care professionals associated with the selected provider location, and the list of diagnosis codes and the list of treatment codes associated with the selected provider location via the Internet.

31. A method of managing healthcare provider data and preparation and settlement of healthcare provider claims as described in claim 14, wherein the enterprise server is maintained at a physical location operated by the third party payer.

\* \* \* \* \*